United States Patent [19]

Jolles

[11] 3,957,755
[45] May 18, 1976

[54] NAPHTHACENE DERIVATIVES
[75] Inventor: Georges Jolles, Sceaux, France
[73] Assignee: Rhone-Poulenc S.A., Paris, France
[22] Filed: Oct. 7, 1971
[21] Appl. No.: 187,559

Related U.S. Application Data
[63] Continuation-in-part of Ser. No. 768,532, Oct. 17, 1968, abandoned.

[30] Foreign Application Priority Data
Oct. 18, 1967  United Kingdom............ 124943/67
Sept. 19, 1968  Finland............................... 2648/68
Oct. 11, 1968  Finland............................. 14582/68
Oct. 16, 1968  Finland........................... 203181/68
Oct. 16, 1968  Finland............................. 38326/68
Oct. 16, 1968  Finland........................... 106490/68
Oct. 17, 1968  Japan................................ 43-75538
Oct. 17, 1968  Japan................................... 43-494
Oct. 18, 1967  France............................ 67.124943

[52] U.S. Cl............................. 260/210 R; 424/180
[51] Int. Cl.² .......................................... C07H 15/00
[58] Field of Search................... 260/210 R, 210 AB

[56]  References Cited
UNITED STATES PATENTS
3,590,028  6/1971  Arcamone et al............ 260/210 AB
3,686,163  8/1972  Arcamone et al............ 260/210 AB

*Primary Examiner*—Johnnie R. Brown
*Attorney, Agent, or Firm*—Stevens, Davis, Miller & Mosher

[57] ABSTRACT

Naphthacene derivatives of the formula:

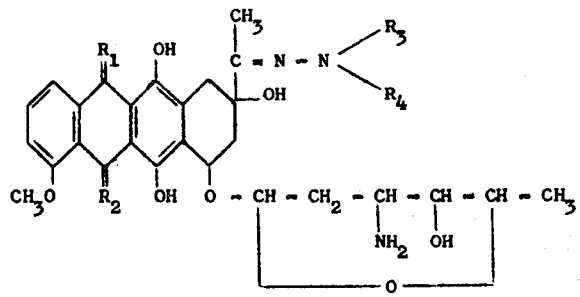

wherein each of $R_1$ and $R_2$ represents an oxygen atom or a group of the formula

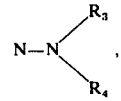

and $R_3$ represents hydrogen, or an alkyl, alkanoyl, thioalkanoyl, aryl, aroyl, carbamoyl, thiocarbamoyl, methylthiocarbamoyl or amidino group, these groups being optionally substituted, and $R_4$ represents hydrogen, or $R_3$ and $R_4$ together with the nitrogen atom to which they are attached represent piperazin-1-yl which carries on the second nitrogen atom an optionally substituted alkyl group, and non-toxic salts thereof, possess anti-tumor properties.

10 Claims, No Drawings

NAPHTHACENE DERIVATIVES

This application is a Continuation-in-Part of our Application Ser. No. 768532 filed Oct. 17th 1968, and now abandoned.

THIS INVENTION relates to new therapeutically useful naphthacene derivatives, to a process for their preparation and pharmaceutical compositions containing them.

According to the present invention, there are provided the new naphthacene derivatives of the general formula:-

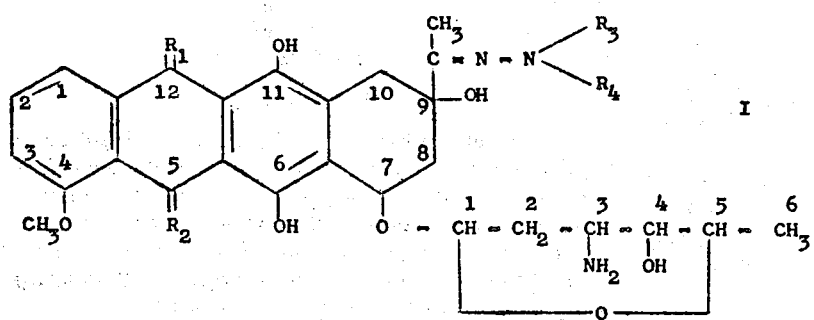

wherein $R_1$ and $R_2$ are the same or different and each represents an oxygen atom or a group of the formula

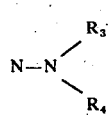

and $R_3$ represents a hydrogen atom or an alkyl, alkanoyl, thioalkanoyl, aryl (e.g. phenyl), aroyl (e.g. benzoyl), carbamoyl, thiocarbamoyl, methylthiocarbamoyl or amidino group, these groups being optionally substituted, and $R_4$ represents a hydrogen atom, or $R_3$ and $R_4$ together with the nitrogen atom to which they are attached represent a piperazin-1-yl group wich carries on the second nitrogen atom an optionally substituted alkyl group and salts thereof. The substituents which may be present on the groups $R_3$ and on the alkyl group in the 4-position of the piperazinyl ring when

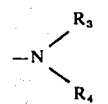

represents a 4-alkylpiperazin-1-yl group are preferably substituents of acid or basic character which are able to improve the solubility of the naphthacene derivatives of formula I in water. Preferably the substituents are quaternary ammomium and sulphonic acid groups, or residues of amino acids and of peptides. The alkyl, alkanoyl and thioalkanoyl groups mentioned above preferably contain at most 4 carbon atoms.

According to a feature of the present invention, the naphthacene derivatives of general formula I are prepared by reacting a compound of the general formula:-

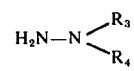

with the naphthacene derivative of the formula:-

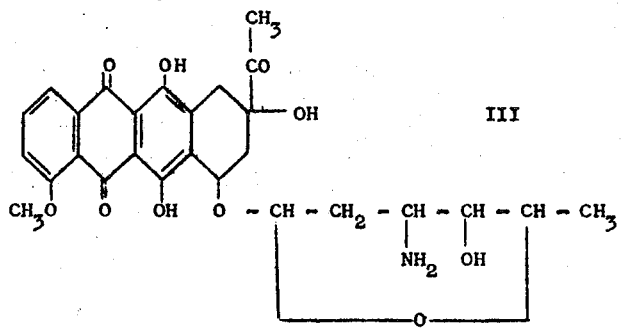

or acid addition salt thereof. The reaction is carried out under the usual conditions for the conversion of ketones to hydrazono compounds, and is preferably effected in an inert organic solvent, such as an alcohol (e.g. ethanol) or dimethylformamide, with gentle heating.

When it is desired to obtain a naphthacene product of formula I wherein $R_1$ or $R_2$ represents a group

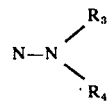

or $R_1$ and $R_2$ both represent groups

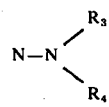

two moles or three moles of the starting material of formula II are required, respectively, for each mole of the naphthacene compound of formula III.

The napthacene derivative of formula III is the antibiotic designated by the number 13,057 R.P., which has bee given the name "daunorubicin". Its preparation and physico-chemical properties have been described in British Pat. No. 985,598 granted to Rhone-Poulenc S.A. on an application filed May 16, 1963. In earlier publications it has been called "rubidomycin".

The naphthacene derivatives prepared by the aforementioned process may, where appropriate, be converted into acid addition salts or salts with nitrogen-containing bases, into metal salts or into quaternary ammonium salts. The salts may be obtained by the reaction of the naphthacene derivatives of formula I with acids or bases in appropriate solvents. As organic solvents there may be used, for example, alcohols, ethers, ketones or chlorinated hydrocarbons. The salt which is formed is precipitated, if necessary after concentration of its solution, and is separated by filtration or decantation. The quaternary ammonium salts may be obtained by the reaction of esters on the naphthacene bases, optionally in an organic solvent, at room temperature or more rapidly with gentle heating.

The naphthacene derivatives of general formula I and their salts have interesting anti-tumor properties, combined with a low toxicity. They have proved particularly active against leukaemia L1210 (administered intra-peritoneally) in mice. The experiments were carried out on 1 month old mice weighing 18 to 20 grams intra-peritoneally grafted with $10^3$ leukaemia L1210 cells and treated with doses of the naphthacene derivative between 0.5 and 5 mg/kg. (i.p.). Preferred compounds of formula I are those wherein the symbol $R_3$ represents an alkanoyl group optionally carrying a sulphonic acid or quaternary ammonium (e.g. $(CH_3)_3N^+Cl^-$) group, or a thiocarbamoyl, methylthiocarbamoyl or amidino group, and salts thereof. Of outstanding importance are 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydronaphthacene, 4-methoxy-5- (or 12-) oxo-6,9,11-trihydroxy-7-(2,3,6 -O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene, 4-methoxy-5,12-dioxo-6,9,11-trihydroxy-7 -(2,3,6-O-tridesoxy-3-amino-1-L-lyxohexosyl)-9-[1-(4-methylthiosemicarbazono)ethyl]-5,7,8,9,10,12-hexahydro-naphthacene, and 4-methoxy-5,12-dioxo-6,9,11-trihydroxy-7-(2,3,6-O-tridesoxy)-3-amino-1-L-lyxohexosyl)-9-[1-(benzoylhydrazono)ethyl]-5,7,8,9,10,12-hexahydronaphthacene.

The naphthacene derivatives of formula I may be employed as such or in the form of non-toxic salts, i.e. salts containing ions which are relatively innocuous to the animal organism in therapeutic doses of the salts, such as hydrochlorides, sulphates, nitrates, phosphates, acetates, propionates, succinates, benzoates, fumarates, maleates, tartrates, theophylline-acetates, salicylates, phenolphthalinates or methylene-bis-$\beta$-hydroxynaphthoates), metal salts such as the sodium salts, or salts with nitrogen-containing bases. They may also be employed in the form of non-toxic quaternary ammonium salts obtained by reaction of the naphthacene derivatives with organic halides, e.g. methyl, ethyl, allyl or benzyl chloride, bromide or iodide, or other reactive esters, e.g. methyl- or ethyl- sulphates, benzene sulphonates or toluene-p-sulphonates.

The following Examples, in which the percentage yields obtained are related to the theoretical yield, illustrate the invention.

EXAMPLE 1

Daunorubicin hydrochloride (0.5 g.) is dissolved in a mixture of dimethylformamide (20 cc.) and water (10 cc.). Sodium 2-aminocarbamoyl-ethanesulphonate (0.42 g.) is added. The mixture is stirred for 24 hours at ambient temperature, evaporated to dryness under reduced pressure (25 mm.Hg), and the resulting residue taken up in water (100 cc.).

A slight amount of insoluble matter is filtered off and the filtrate then lyophilised. The sodium salt of 4-methoxy-5- (or 12-) oxo-6,9,11-trihydroxy-7-(2,3,6-O-tridesoxy-3-amino-1-L-lyxohexosyl)-9-[1-(3-sulphopropionylhydrazono)ethyl]-12- (or 5-) (3-sulpho-propionylhydrazono)-5,7,8,9,10,12-hexahydro-naphthacene (0.875 g.) is thus obtained in a yield of 95%.
S % : 7.47 (theory: 7.36). N % 7.7 (theory: 8.03)
Ultra-violet spectrum:
 $\lambda$ max = 233 nm ; $\epsilon$ = 29,200
 $\lambda$ max = 252 nm ; $\epsilon$ = 20,920
 $\lambda$ max = 288 nm ; $\epsilon$ = 6,100

EXAMPLE 2

Daunorubicin hydrochloride (0.6 g.) is dissolved in ethanol (65 cc.) containing 2.5% of acetic acid, and Girard reagent T (0.369 g.) is added. The mixture is heated for 4 hours at 40°C. with stirring, evaporated to dryness under reduced pressure (25 mm.Hg), and the resulting residue taken up in water (50 cc.).

A slight amount of insoluble matter is filtered off and the filtrate is lyophilized. 4-Methoxy-5- (or 12-) oxo-6,9,11-trihydroxy-7-(2,3,6-O-tridesoxy-3-amino-1-L-lyohexosyl)-9-[1-(trimethylammonioacetylhydrazono)ethyl]-12- (or 5-) (trimethylammonioacetylhydrazono)-5,7,8,9,10,12-hexahydro-naphthacene dichloride hydrochloride (0.855 g.) is thus obtained.
Cl % : 12.07 (theory : 12.32)
Ultra-violet spectrum :
 $\lambda$ max = 233 nm ; $\epsilon$ = 38,200
 $\lambda$ max = 252 nm ; $\epsilon$ = 27,500
 $\lambda$ max = 290 nm ; $\epsilon$ = 7,720

EXAMPLE 3

Daunorubicin hydrochloride (0.5 g.) is dissolved in ethanol (80 cc.) containing 2.5% of acetic acid. Thiosemicarbazide (0.084 g.) is added and the mixture heated for 4 hours at 40°C. with stirring. It is then stirred for 72 hours at ambient temperature, evaporated to dryness under reduced pressure (25 mm.Hg) and the dry residue taken up in water (80 cc.).

A slight amount of insoluble matter is filtered off and the filtrate then lyophilized to give 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydro-naphthacene hydrochloride (0.483 g.).
N % : 8.85 (theory : 8.79) S % : 5.0 (theory : 5.03).
Ultra-violet spectrum :
 $\lambda$ max = 232 nm ; $\epsilon$ = 32,250
 $\lambda$ max = 257 nm ; $\epsilon$ = 32,225.

EXAMPLE 4

Daunorubicin hydrochloride (0.6 g.) is dissolved in ethanol (30 cc.) containing 2.5% of acetic acid. A solution of aminoguanidine (0.151 g.) in N hydrochloric acid (1.09 cc.) is prepared separately. The two solutions are mixed and heated at 50°C. for 4 hours; the mixture is then left for 72 hours at ambient temperature and thereafter evaporated to dryness under reduced pressure (25 mm.Hg). The residue is taken up in water (60 cc.), a slight amount of insoluble matter is filtered off and the filtrate is lyophilized. 4-Methoxy-5,12-dioxo-6,9,11-trihydroxy-7-(2,3,6-O-tridesoxy-3-amino-1-L-lyxohexosyl)-9[1-(amidinohydrazono)-ethyl]-5,7,8,9,10,12-hexahydro-naphthacene dihydrochloride (0.64 g.) is thus obtained.
N % : 10.73 (theory : 10.66)
Ultra-violet spectrum :
 $\lambda$ max = 233 nm ; $\epsilon$ = 45,500
 $\lambda$ max = 253 nm ; $\epsilon$ = 27,820
 $\lambda$ max = 291 nm ; $\epsilon$ = 8,515

EXAMPLE 5

Daunorubicin hydrochloride (0.4 g.) is dissolved in ethanol (60 cc.) containing 2.5% of acetic acid, and thiosemicarbazide (0.135 g.) is then added. The resulting mixture is heated for 12 hours to 45°C. with stirring, then evaporated to dryness under reduced pressure, and the residue is taken up in water (50 cc.). The resulting solution is lyophilized to give 4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene hydrochloride (0.476 g.) in a yield of 89%.

Cl % : 4.97 (theory : 4.99. S% : 8.90 (theory : 9.02).
Ultra-violet spectrum:
$\lambda$ max = 233 nm ; $\epsilon$ = 42,000
$\lambda$ max = 257 nm ; $\epsilon$ = 31,800.

EXAMPLE 6.

Daunorubicin hydrochloride (10 g.) is dissolved in methanol (1500 cm$^3$) and benzene (150 cm$^3$) and 4-methylthiosemicarbazide (2.05 g) added. The reaction medium is concentrated by distilling off 200 cm$^3$ of solvent, and heated with shaking at 60°C for 24 hours; it is then evaporated to dryness under reduced pressure (25 mm of mercury) at 45°C. The residue is extracted by shaking vigorously with diethyl ether (2000 cm$^3$). The resulting precipitate is filtered off, washed with a 1:3 mixture (by volume) of methanol/ether and dried under reduced pressure (0.3 mm of mercury) at 20°C. The precipitate is taken up with distilled water and lyophilized. 4-methoxy-5,12-dioxo-6,9,11-trihydroxy-7-(2,3,6-O-tridesoxy-3-amino-1-L-lyxohexosyl)-9-[1-(4-methylthiosemicarbazono)ethyl]-5,7,8,9,-10,12-hexahydro-naphtacene hydrochloride (10.8 g) is obtained. N % = 8.45 (theory = 8.60) S% = 4.89 (theory = 4.92)

The 4-methylthiosemicarbazide is prepared by the method of G.PULVERMACHER, Ber., 27, 613 (1894).

EXAMPLE 7

Daunorubicin hydrochloride (9.024 g) is dissolved in ethanol (800 cm$^3$) containing 2.5% acetic acid and benzoylhydrazide (2.162 g) added. The mixture is heated for 24 hours at 60°C and the resulting precipitate is filtered off, washed with ethanol (100 cm$^3$), and dried under reduced pressure (0.3 mm of mercury) at 20°C. The precipitate is taken up with distilled water, filtered to remove a slight precipitate, and lyophilized. 4-Methoxy-5,12-dioxo-6,9-11-trihydroxy-7-(2,3,6-O-tridesoxy-3 amino-1-L-lyxohexosyl)-9-[1-benzoylhydrazono-ethyl]-5,7,8,9,10,12-hexahydro-naphthacene hydrochloride((10.17 g) is obtained. N % = 5.87 (theory = 6.16).

The benzoylhydrazide is prepared by the method of B. Rogers et al., U.S. Atomic Energy Comm. L.A. 1639 (1953) [C.A. 49, 7559 i (1955)].

The present invention includes within its scope pharmaceutical compositions which comprise at least one of the naphthacene derivatives of general formula I, or a non-toxic salt thereof, in association with a pharmaceutically-acceptable carrier or coating. In clinical practice the compounds of the present invention will normally be administered parenterally.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilising agents, by irradiation, or by heating. They may also be manufactured in the form of sterile solid compositions, which can be dissolved or dispersed in sterile water or some other sterile injectable medium immediately before use.

The percentage of active ingredient in the compositions of the invention may be varied, it being necessary that it should constitute a proportion such that a suitable dosage shall be obtained. The dosage will depend upon the therapeutic effect sought, the length of treatment, and the species of animal. In human therapy, for example in the treatment of the lymphoblastic and myeloblastic forms of acute leukaemia, and chronic myeloid leukaemia, the compositions should generally be administered so as to give, in the case of parenteral administration, doses between 2 and 10 mg./kg. of naphthacene derivative per day for an adult.

The following Example illustrates pharmaceutical compositions according to the invention.

EXAMPLE 8

A solution of the following composition is prepared:
4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-1) (thiosemicarbazono)-5,7,8,9,10,12-hexahydronaphthacene hydrochloride   2.1 g.
distilled water   100 cc.

This solution is sterilised by filtering through a bacteriostatic filter and is then divided between ampoules in a quantity of 10 cc. per ampoule. The ampoules are thereafter lyophilized under a nitrogen atmosphere and sealed.

For parenteral administration as a medicine, an injectable solution is prepared immediately before use by adding 5 cc. of physiological serum to the contents of the ampoule. A 5 cc. solution containing 200 mg. of active product is thus obtained.

I claim:
1. A naphthacene of the formula:

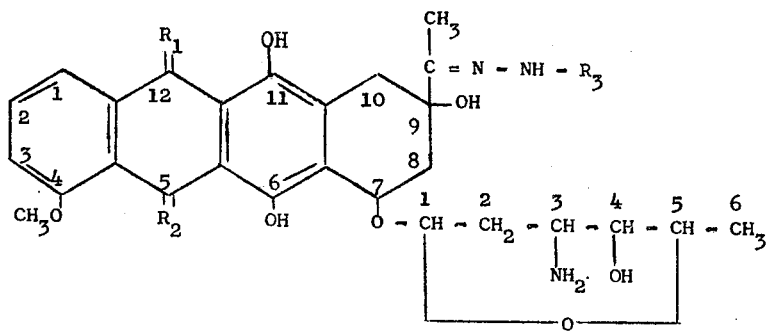

wherein one of $R_1$ and $R_2$ is oxygen and the other is oxygen or $:N - NHR_3$, and $R_3$ is alkanoyl of up to 4 carbon atoms, alkanoyl of up to 4 carbon atoms substituted by a sulphonic acid group, alkanoyl of up to 4 carbon atoms substituted by a quaternary ammonium group, thiocarbamoyl, methylthiocarbamoyl amidino, or benzoyl, and non-toxic salts thereof.

2. A naphthacene of the formula:

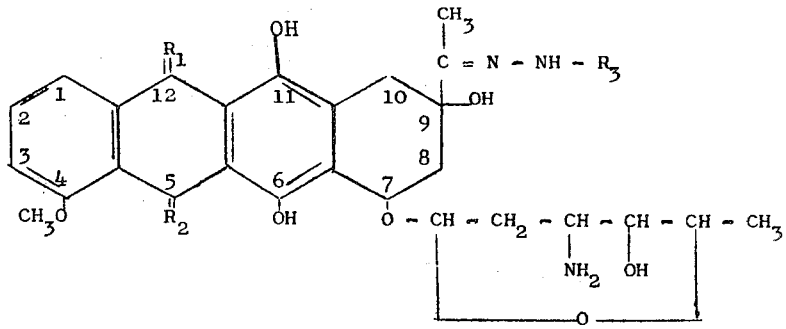

wherein one of $R_1$ and $R_2$ is oxygen and the other is oxygen or $:N - NHR_3$, and $R_3$ is alkanoyl of up to 4 carbon atom, alkanoyl of up to 4 carbon atoms substituted by a sulphonic acid group, alkanoyl of up to 4 carbon atoms substituted by a quaternary ammonium group, thiocarbamoyl, amidino, or benzoyl, and non-toxic salts thereof.

3. The naphthacene derivative according to claim 1 which is 4-methoxy-5- (or 12-) oxo-6,9,11-trihydroxy-7-(2,3,6-O-tridesoxy-3-amino-1-L-lyxohexosyl)-9-[1-(3-sulpho-propionylhydrazono)ethyl]-12- (or 5-) (3-sulpho-propionylhydrazono)-5,7,8,9,10,12-hexahydro-naphthacene, and non-toxic acid addition and non-toxic metal salts thereof.

4. The naphthacene derivative according to claim 1 which is 4-methoxy-5- (or 12-) oxo-6,9,11-trihydroxy-7-(2,3,6-O-tridesoxy-3-amino-1-L-lyxohexosyl)-9-[1-(trimethylammonioacetylhydrazono)ethyl]-12- (or 5-) (trimethylammonioacetylhydrazono)-5,7,8,9,10,12-hexahydro naphthacene dichloride, and non-toxic acid addition salts thereof.

5. The naphthacene derivatives according to claim 1 which is 4-methoxy-5,12-dioxo-6,9,11-trihydroxy-7-(2,3,6-O-tridesoxy-3-amino-1-L-lyxohexosyl)-9-[1-(thiosemicarbazono)ethyl]-5,7,8,9,10,12-hexahydronaphthacene, and non-toxic acid addition salts thereof.

6. The naphthacene derivative according to claim 1 which is 4-methoxy-5,12-dioxo-6,9,11-trihydroxy-7-(2,3,6-O-tridesoxy-3-amino-1-L-lyxohexosyl)-9-[1-(amidinohydrazono)ethyl]-5,7,8,9,10,12-hexahydronaphthacene, and non-toxic addition salts thereof.

7. The naphthacene derivative according to claim 1 which is 4-methoxy-5- (or 12-) oxo-6,9,11-trihydroxy-7-(2,3,6-O-tridesoxy-3-amino-1-L-lyxohexosyl)-9-[1-(thiosemicarbazono)ethyl]-12- (or 5-) (thiosemicarbazono)-5,7,8,9,10,12-hexahydro-naphthacene, and non-toxic acid addition salts thereof.

8. The naphthacene derivative according to claim 2 which is 4-methoxy-5,12-dioxo-6,9,11-trihydroxy-7-(2,3,6-O-tridesoxy-3-amino-1-L-lyxohexosyl)-9-[1-(4-methylthiosemicarbazono)ethyl]-5,7,8,9,10,12-hexahydro-naphthacene and non-toxic acid addition salts thereof.

9. The naphthacene derivative according to claim 1 which is 4-methoxy-5,12-dioxo-6,9,11-trihydroxy-7-(2,3,6-O-tridesoxy-3-amino-1-L-lyxohexosyl)-9-[1-(benzoylhydrazono)ethyl]-5,7,8,9,10,12-hexahydronaphthacene and non-toxic acid addition salts thereof.

10. A naphthacene according to claim 1 in which $R_1$ and $R_2$ are both oxygen and $R_3$ is alkanoyl of up to 4 carbon atoms or benzoyl, and non-toxic salts thereof.

* * * * *

UNITED STATES PATENT OFFICE
CERTIFICATE OF CORRECTION

Patent No. 3,957,755          Dated May 18, 1976

Inventor(s) Georges JOLLES

It is certified that error appears in the above-identified patent and that said Letters Patent are hereby corrected as shown below:

In the heading "[30] Foreign Application Priority Data", delete the references to the first eight foreign applications, leaving only the foreign application priority data for the French Application as it appears as the ninth item in the present listing.

France 67.124943     October 18, 1967

Signed and Sealed this

Twenty-eighth Day of September 1976

[SEAL]

Attest:

RUTH C. MASON
*Attesting Officer*

C. MARSHALL DANN
*Commissioner of Patents and Trademarks*